US005433221A

United States Patent [19]
Adair

[11] Patent Number: 5,433,221
[45] Date of Patent: Jul. 18, 1995

[54] WINDOWED SELF-CENTERING DRAPE FOR SURGICAL CAMERA

[76] Inventor: Edwin L. Adair, 317 Paragon Way, Castle Pines Village, Colo. 80104

[21] Appl. No.: 318,271

[22] Filed: Oct. 5, 1994

[51] Int. Cl.$^6$ .............................................. A61B 19/00
[52] U.S. Cl. .................................. 128/849; 128/853; 128/856; 359/510
[58] Field of Search ................... 128/849–856; 206/330, 438; 358/98, 229; 359/510, 511, 900; 354/62

[56] References Cited

U.S. PATENT DOCUMENTS

| | | | |
|---|---|---|---|
| Re. 34,002 | 7/1992 | Adair | 358/229 |
| 4,183,613 | 1/1980 | Walchle | 359/510 |
| 4,266,663 | 5/1981 | Geraci | 359/510 |
| 4,308,864 | 1/1982 | Small | 128/856 |
| 4,561,540 | 12/1985 | Hunter | 359/510 |
| 4,745,915 | 5/1988 | Enright | 128/853 |
| 4,887,615 | 12/1989 | Taylor | 128/856 |
| 4,914,521 | 4/1990 | Adair | 358/229 |
| 4,998,538 | 3/1991 | Cherowsky | 128/856 |
| 5,078,483 | 1/1992 | Herzberg | 359/510 |
| 5,178,162 | 1/1993 | Bose | 128/856 |
| 5,198,894 | 3/1993 | Hicks | 358/98 |
| 5,237,984 | 8/1993 | Williams, III et al. | 128/4 |
| 5,274,500 | 12/1993 | Dunn | 359/507 |
| 5,325,846 | 7/1994 | Szabo | 128/4 |

*Primary Examiner*—Michael A. Brown
*Attorney, Agent, or Firm*—Fields, Lewis, Rost & Smith

[57] ABSTRACT

In accordance with this invention, a windowed self-centering drape for a surgical camera is provided. The drape includes a generally cylindrical body portion and a flexible and elastic distal end. The body portion is flexible and substantially non-elastic. The proximal end of the body portion may include either a roll fold or an accordion fold in order to reduce the size of the drape for storage prior to use. An optically clear window is formed integrally with the elastic distal end. The window may be coated with substances which filter out certain wavelengths of light.

8 Claims, 4 Drawing Sheets

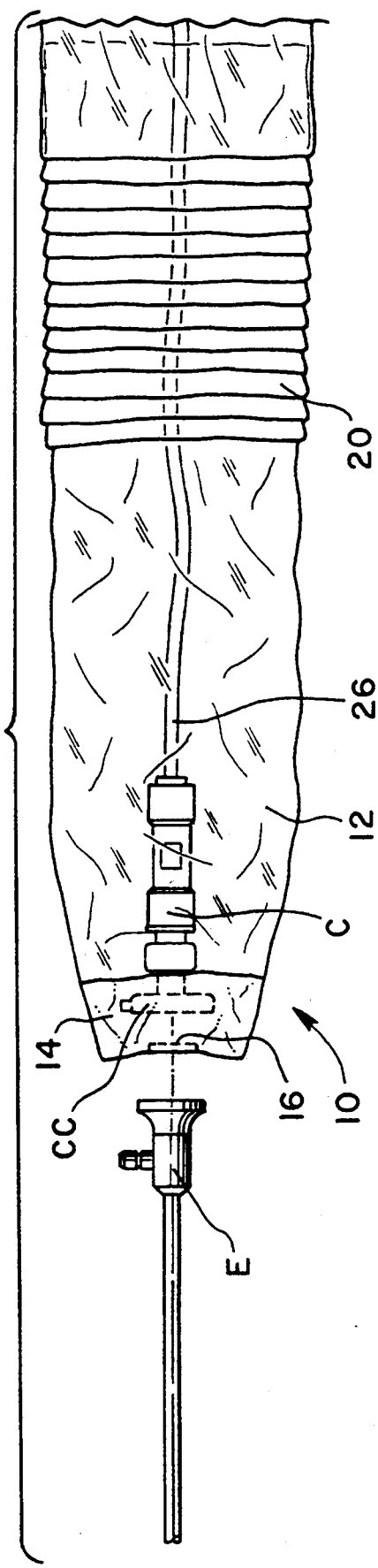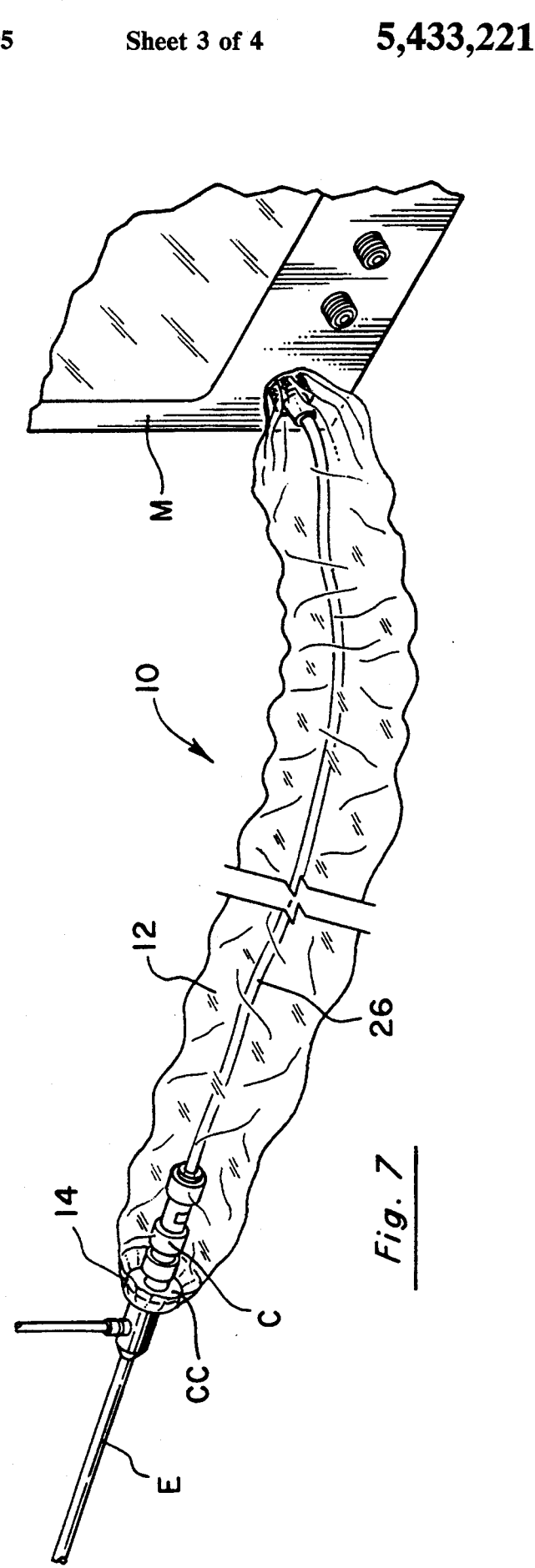

WINDOWED SELF-CENTERING DRAPE FOR SURGICAL CAMERA

TECHNICAL FIELD

This invention relates to sterile drape for covering a surgical camera and its trailing cables for use in an operating room.

BACKGROUND ART

It is common in the art for unsterile cameras used in surgical procedures to be enclosed by some type of sterile drape. The sterile drape allows the camera to be coupled with an endoscope or other surgical device without compromising operating room sterility. Most commonly, the prior art discloses surgical drapes which are made of a single type of material, such as polyethylene, with a window located at the distal end where a camera coupler is positioned and couples to the endoscope. One major disadvantage with devices of this type is that it is extremely difficult to obtain the proper alignment of the drape between the camera coupler and the endoscope to ensure an optically clear path. The drape can become folded or otherwise caught in the connection between the camera coupler and endoscope thus blocking the window and obstructing the optical path. Also, polyethylene and other similar materials do not stretch without permanent deformation, thus compromising the integrity of a sterile drape made of such material. That is, adjustments in aligning the window with the optical path can result in a tear or other damaging deformation of the drape. Additionally, because of the difficulty in obtaining proper window alignment, excessive handling by operating room personnel may ensue causing inadvertent contamination of the sterile endoscope or sterile drape.

Another common shortfall in the prior art is that the conventional window is not made of a high quality, optically clear material. Additionally, such windows generally transmit laser light effectively, resulting in projection of high intensity laser light onto the CCD image sensor of the camera. This laser light can be of such high intensity that it can "blank out" a video screen used to view the surgical area. Use of laser energy for coagulation and cutting thus creates a need for some type of band pass filter on the window to filter out undesirable wavelengths of light.

Typical of the prior art devices include U.S. Pat. No. 5,274,500 to Dunn which teaches a surgical drape for a video camera device providing a sealed, sterile encasement of the camera and its associated transmission cables. This device includes a flexible tubular member and a distal end including a lens which allows the camera to be optically coupled with an endoscope.

U.S. Pat. No. 5,078,483 to Herzberg teaches a sterile disposable camera cover made from a tubular film folded onto itself and forming a package including a plurality of folded layers. One end of the camera extends into and through an end portion of the cover so that both ends of the cover are co-located at the same side of a film package which houses the cover prior to use.

U.S. Pat. No. 5,198,894 to Hicks discloses an endoscope having a sleeve-like drape secured in a retracted position at the proximal end of the endoscope. When the endoscope is secured to a camera, the drape is extended to telescope over and envelope the camera such that the resulting outer surface of the drape in its extended position remains sterile. The drape is attached at the proximal end of the endoscope as opposed being positioned between the camera and the endoscope.

A particularly relevant prior art reference is my earlier U.S. Patent No. Re. 34,002. The invention disclosed therein includes a sterile drape which extends over the camera and its extending cables, and a connecting structure which allows the video camera to be attached to an optical connector known in the art as a "C" mount or "V" mount.

It is one primary object to provide for a sterile drape having an elastic distal segment that results in easier alignment of the window when connecting a camera to an endoscope, and prevents damage to the drape, the elastic material being able to withstand the stress of the physical connection between a camera and endoscope. It is another object of this invention to provide for a window that may be coated with a material that results in filtering certain wavelengths of light passing therethrough. These coatings are particularly important when laser light is used during the surgical procedure. It is yet another object of this invention to provide for a window being constructed of an optically clear and durable material that does not easily cloud or damage, thus enhancing the ability of light to pass undistorted therethrough.

While the prior references may be adequate for their intended purposes, none of the references show either alone or in combination the novel structure set forth below.

DISCLOSURE OF THE INVENTION

An apparatus is provided for enclosing an unsterile video camera and its trailing cables for use in the sterile environment of an operating room. The apparatus includes a generally cylindrical body portion made of a flexible and impervious material such as polyethylene. Connected to the body portion is a distal end constructed of an elastic material such as polyurethane. A commercially available polyurethane of this type is 'Elasto Flex K' or 'Elasto Flex 3' manufactured by Clopay Corp., Cincinnati, Ohio. A window portion is formed integrally with the elastic distal end. The window may be constructed of polycarbonate which is an optically clear material having exceptional durability, strength, and resistance to scratching or other damage. Other materials having similar characteristics advantageous for use in the window are PETG, styrene or acrylic. Typically, the window is heat sealed to the distal polyurethane end, thus providing a leak proof seal. Similarly, the polyethylene body portion is also heat sealed to the distal polyurethane end, or attached by other suitable methods. Prior to use, the body portion is folded at its proximal end in either an accordion-fold configuration or a rolled configuration. An adhesive strip may be positioned on the proximal end of the body portion enabling one to secure it to a surface such as the trailing camera cable when the drape is fully extended during use.

A non-sterile video camera and camera coupler are inserted within the interior of the apparatus with the camera coupler coming in contact with the drape window. A sterile endoscope is then coupled to the camera coupler wherein the window acts as an optically clear and sterile barrier. A camera coupler typically includes a first end having a recess for receiving an endoscope and a second end having threads or a compression fitting for receiving a camera. Depending upon the type of camera and endoscope, the coupler may also include a series of lenses or a window positioned inside the coupler housing. When attaching the endoscope to the camera coupler, the window is held in place by the endoscope eyepiece while the connection is made. The elastic material surrounding the window allows it to be pressed down inside the recess within the first end of the coupler, the eyepiece causing the drape window to "seat" against a lens inside of the coupler. Thus, during the attaching process, the elastic material is deformed to follow the shape of the connecting elements and allows the window to be more easily centered in the optical path between the coupler and endoscope. This deformation in conventional drapes often times results in slippage of the window causing it to move off center or damaging the elastic drape which becomes permanently deformed. When centering the window of the invention disclosed herein, tension may be placed on the elastic material around the periphery of the window without tearing or otherwise degrading the integrity of the drape itself. The elastic material has "memory" which means it returns to its undeformed shaped after being stretched during use. The ability to manipulate the location of the window without fear of drape degradation greatly eases the alignment of the window along the optical path and contributes to efficient operating room procedures. Additionally, the elastic material is of a somewhat heavier construction than the body portion which helps eliminate the creation of folds that might become caught in the connection between the camera coupler and endoscope, the heavier construction of the elastic material being less prone to folding or otherwise creating interference.

For applications where laser light is used to illuminate the operating area, the window portion may be coated with an appropriate material to filter out undesirable wavelengths that cause distortion and other problems associated with viewing the image produced on a video screen.

With the apparatus just described, it is possible to provide a sterile drape for an unsterile camera, its associated cables and a camera coupler such that the connection between the endoscope and camera is made simpler and more reliable. A clear and unobstructed optical path between the camera and endoscope is more easily achieved with a window that can be manipulated without the danger of damaging the drape or having the drape caught in the optical path. Operating room procedures are enhanced and sterility problems can be minimized with an apparatus of this type that requires a minimal amount of handling to be put in use.

Additional advantages of this invention will become apparent from the description which follows, taken in conjunction with the accompanying drawings.

BRIEF DESCRIPTIONS OF THE DRAWINGS

FIG. 6 is an exploded side view of the sterile surgical drape of the invention illustrating a camera, its associated cables, and a camera coupler inserted within the drape prior to coupling with an endoscope;

FIG. 7 is a perspective view of the sterile surgical drape of the invention, wherein the camera and endoscope have been coupled with the window portion positioned between the camera coupler and endoscope;

Figure 8:
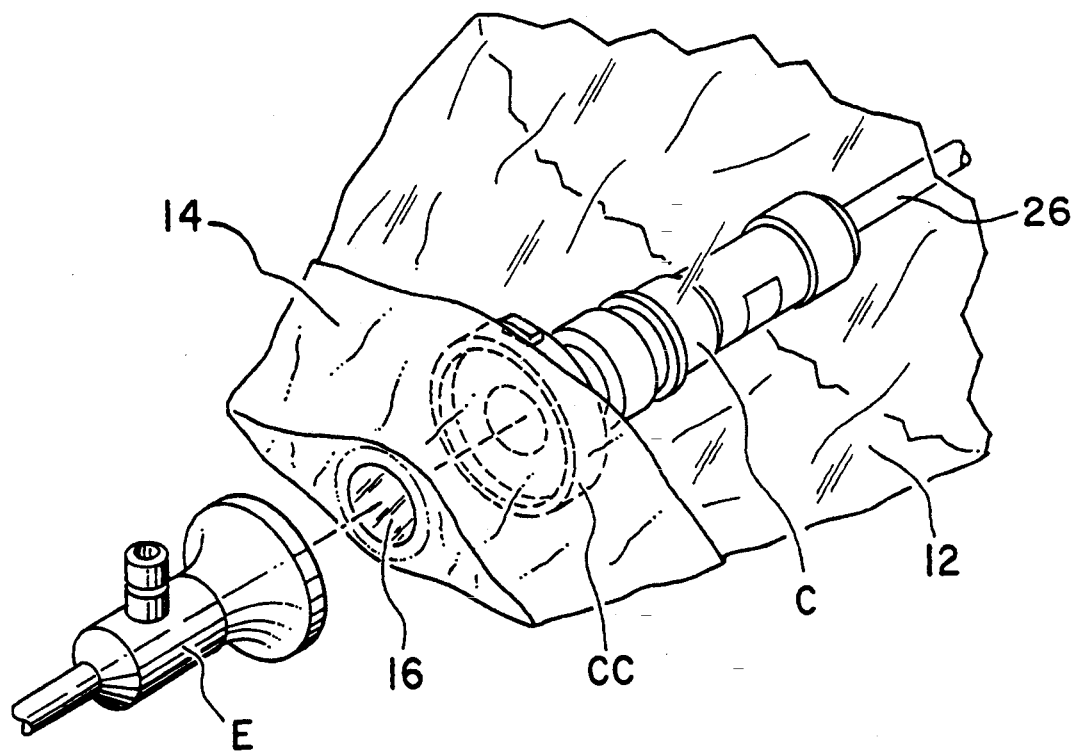
Figure 9:
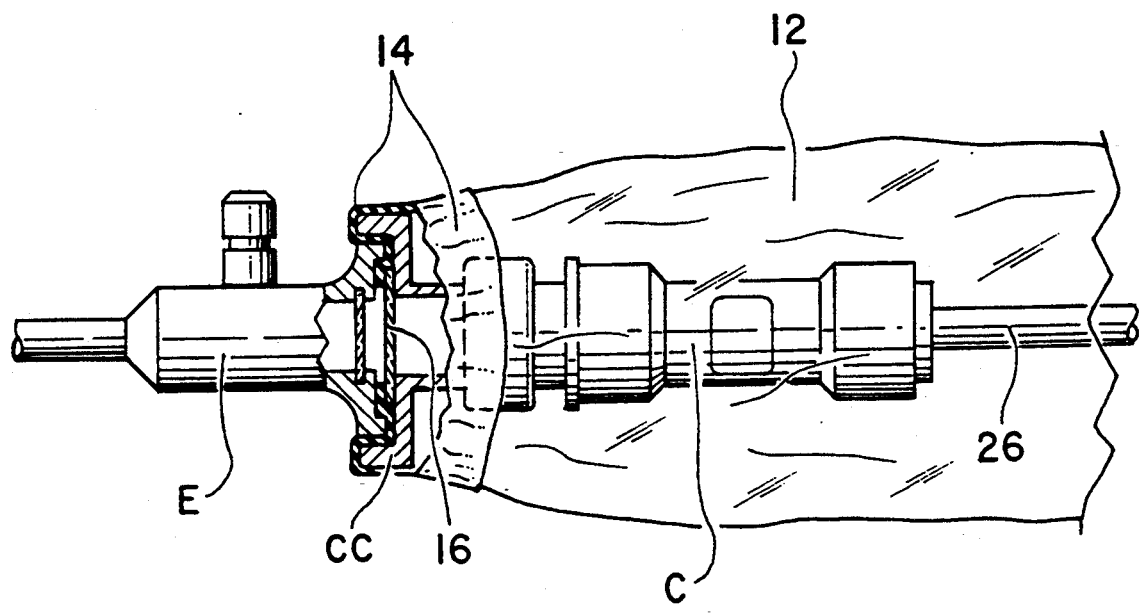

FIG. 8 is an exploded perspective fragmentary view of the sterile surgical drape of the invention illustrating a camera, its associated cables, and a camera coupler inserted within the drape prior to coupling with an endoscope; and FIG. 9 is an enlarged, partial fragmentary, side view of the sterile surgical drape of the invention, wherein the camera and endoscope have been connected with the window portion positioned between the camera coupler and endoscope, and showing the elastic nature of the distal end portion conforming to the connection.

BEST MODE FOR CARRYING OUT THE INVENTION

Figure 1:
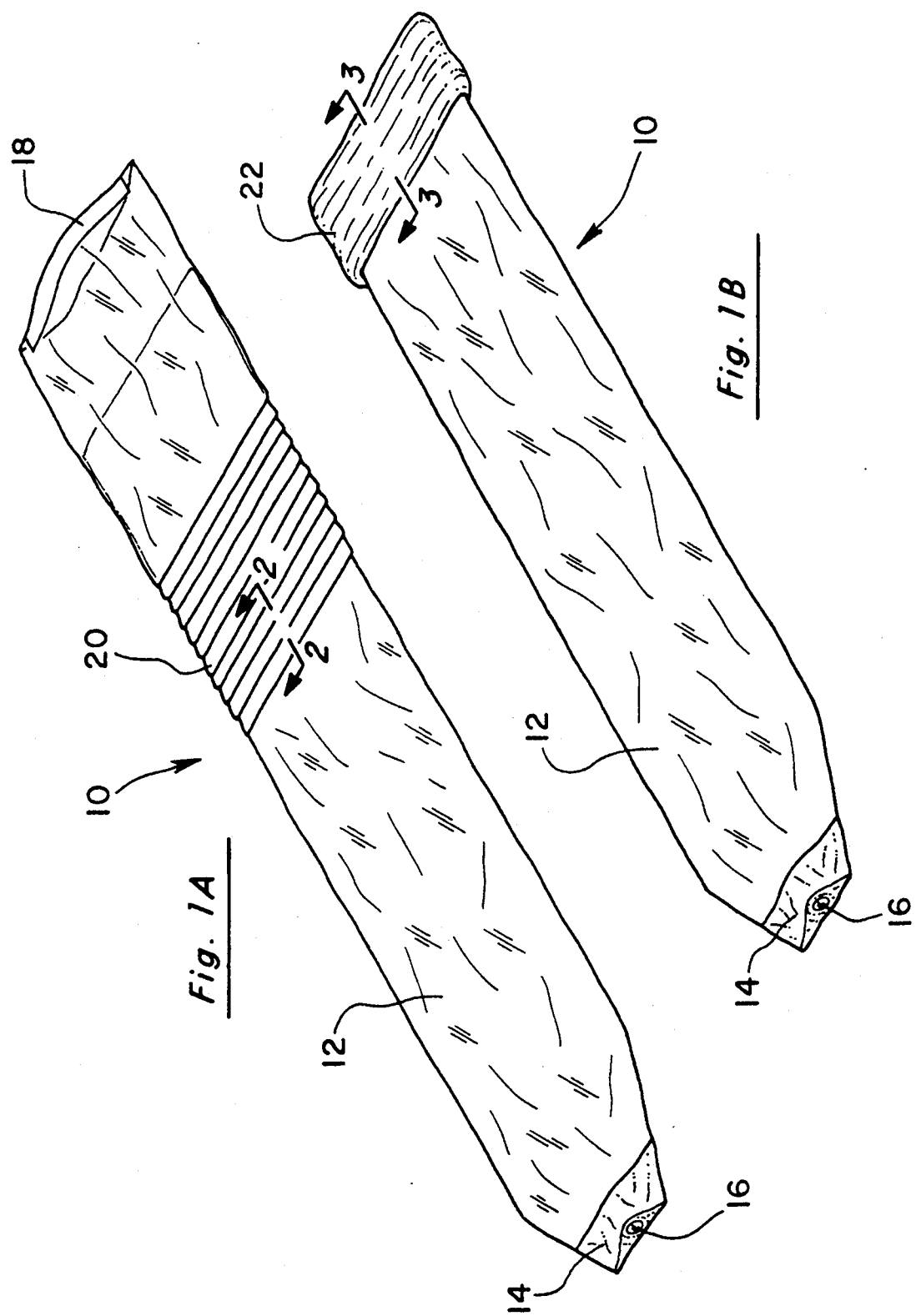
FIG. 1A is a perspective view of one form of the windowed self-centering sterile surgical drape constructed in accordance with this invention, with an accordion fold at its proximal end.
FIG. 1B is a perspective view, similar to FIG. 1A, illustrating an alternative form of the invention with a roll fold.

In accordance with this invention, as best seen in FIG. 1A, a windowed self-centering drape 10 is provided having a flexible and substantially non-elastic body portion 12 and an elastic and flexible distal end portion 14. Body portion 12 is generally cylindrical in shape and has an interior side for receiving a camera C, its trailing cables, and a camera coupler CC. Formed integrally with the elastic distal end 14 is an optically clear window 16. Elastic end portion 14 has a smaller diameter than body portion 12 and includes a generally flat distal tipped edge for mounting the window 16. Window 16 is heat sealed with respect to distal end 14 to form a leak-proof seal. Similarly, body portion 12 is connected to distal end 14 by heat sealing the two elements together. It will be understood that the window 16 can be mounted to the distal end 14 in any number of ways, the only requirement being that there exist a leak-proof seal therebetween.

Figure 2:
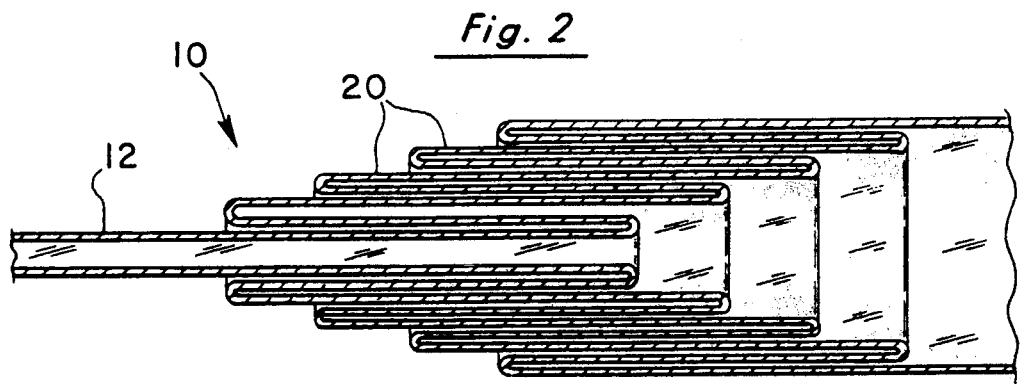
FIG. 2 is a cross-sectional view, taken along line 2—2 of FIG. 1A, showing the construction of the drape with an accordion fold.
Figure 3:
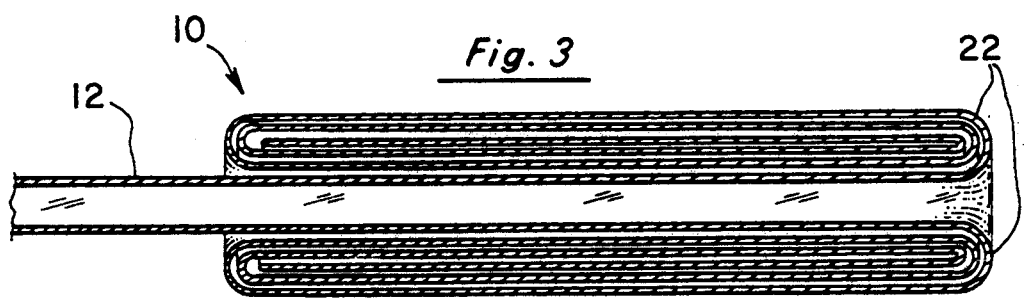
FIG. 3 is a cross-sectional view, taken along line 3—3 of FIG. 1B, showing the construction of the drape with a roll fold.
Figure 4:
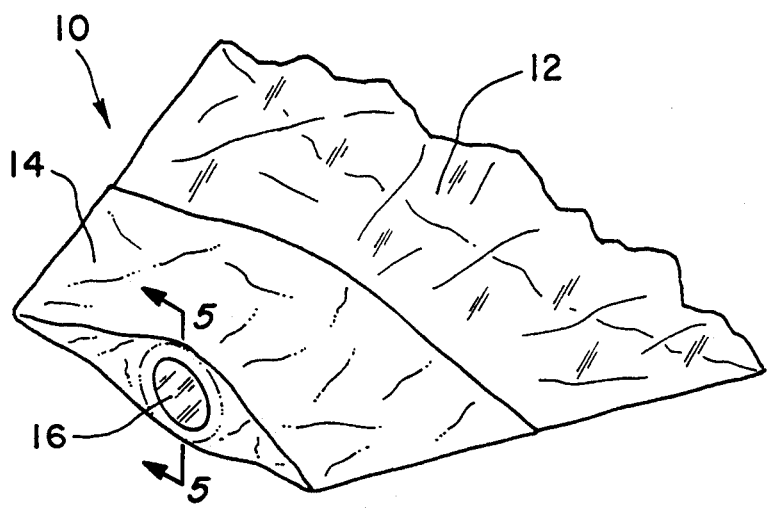
FIG. 4 is an enlarged, fragmentary, perspective view of the elastic distal end and the window portion which is common to each form of the invention.
Figure 5:
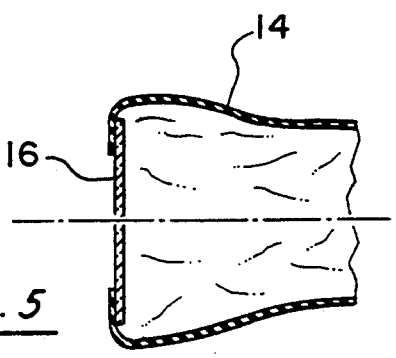
FIG. 5 is an enlarged cross-sectional view, taken along line 5—5 of FIG. 4, illustrating the structural details of the window and elastic distal end.

At the proximal end of body portion 12 is a removable paper strip 18. When removed, paper strip 18 exposes a corresponding length of adhesive strip that can be used to attach the proximal end of the drape to an object such as the proximal end of the camera cable 26 as shown in FIG. 7. The proximal end of body portion 12 may be folded in an accordion manner as is shown by accordion fold 20 in order to reduce the size of the invention for storage prior to use. To extend the drape, one simply grasps the most trailing non-folded end and pulls the drape apart. Alternatively, as shown in FIG. 1B, a roll fold 22 may be used when storing the drape prior to use. The drape in this configuration can be prepared for use by simply unrolling the rolled body portion 12. FIGS. 2 and 3 further illustrate in cross sectional detail the accordion fold 20 and roll fold 22. The number of folds used depends upon how small the drape needs to be for convenient storage. That is, the body portion 12 can be folded or rolled such that the only portion of the drape not encompassed by a fold is the elastic distal end 14.

The window 16 may be coated with a filtering element such that only desirable wavelengths of light are capable of passing therethrough. Application of filters is particularly important when laser light is used during a surgical procedure. The high intensity of a laser can result in a poor image as viewed on a video screen. Alternatively, the window portion can be manufactured with the appropriate amount and type of filtering as is common in the manufacture of polarized lenses.

FIG. 6 shows a camera C with trailing optical cable 26 and camera coupler CC inserted within the drape 10. The window 16 is placed in alignment with camera coupler CC in order that a clear optical path is provided between endoscope E and camera C. Optical cable 26 communicates with viewing monitor M wherein the surgical area may be viewed on the monitor screen.

As shown in FIG. 7, elastic distal end 14 is the portion of the drape 10 which makes contact with the coupler CC. Although FIGS. 6 and 7 illustrate the use of a coupler CC, it will be understood that the drape 10 is equally effective when other types of connections are used to connect an endoscope to a camera. For example, a particular camera manufacturer may have a proprietary coupling system for connection with an endoscope. The elastic distal end 14 lends itself to a wide range of such applications because the window can be centered without fear of undue drape damage or disfiguration.

FIG. 8 illustrates the camera C and coupler CC inserted within the drape, with the coupler CC and endoscope E positioned for attachment.

FIG. 9 shows the elastic distal end 14 conforming to the shape of the connection between the camera coupler CC and endoscope E. As discussed above, the ability of the elastic distal end 14 to stretch and deform to a desired shape substantially eliminates drape damage and results in a self-centering window that is more easily manipulated by surgical personnel.

The operation of the drape 10 can be most simply described as follows:

A drape having folds 20 or 22 is positioned to receive a camera C, its trailing cable 26 and camera coupler CC. The camera C and coupler CC is inserted through the length of the drape 10 such that the camera coupler CC is aligned with the window 16. Coupler CC is then placed in contact with the elastic distal end 14 and the window 16 is pressed inside the recess of coupler CC by the eyepiece of the endoscope E. The connection between the coupler CC and endoscope E is complete when the window 16 is properly seated. The camera C is then connected to the coupler CC. Body portion 12 is pulled back to a length that completely encloses optical cable 26. Paper strip 18 can then be removed in order that the proximal end of the body portion 12 can be secured.

From the foregoing, the advantages of this invention are readily apparent. A windowed self-centering drape has been provided which can be used to provide a sterile covering for a camera and its associated cable. The elastic distal end enables surgical personnel to easily center the window such that an optically clear path is created between the camera and endoscope. The elastic distal end enhances the use of the drape with differing types of equipment used for viewing a surgical area, and substantially reduces the chance that the drape will become damaged from the process of coupling the camera to the endoscope. The optically clear window made of polycarbonate or the like increases the durability of the window and ensures that unnecessary clouding or window damage is reduced. The filtering coating applied to the window allows the desired wavelengths of light to be received by the camera. The accordion fold or roll fold configuration of the body portion enables the drape to be conveniently stored in a relatively small package.

This invention has been described in detail with reference to particular embodiments thereof, but it will be understood that various other modifications can be effected within the spirit and scope of this invention.

I claim:

1. An apparatus for enclosing a non-sterile video camera, its trailing cable, and a camera coupler in a sterile enclosure for use of the camera in the sterile environment of an operating room, the camera being attachable to an endoscope, said apparatus comprising:
   a generally cylindrical body portion having an outer surface, an inner surface with a diameter of a size to receive the camera and coupler, a distal end, and an open proximal end for receiving the camera and coupler, said body portion constructed of a flexible and substantially non-elastic material;
   a distal end portion constructed of a flexible and substantially elastic material attached to said distal end of said body portion; and
   an optically clear window mounted in said distal end portion which is contactable by the camera coupler when positioned inside said body portion for coupling to the endoscope.

2. An apparatus, as claimed in claim 1, wherein said distal end portion is constructed of polyurethane.

3. An apparatus, as claimed in claim 1, wherein said window further includes:
   filter means for selectively filtering wavelengths of light passing through said window.

4. Apparatus, as claimed in claim 1, wherein:
   said window is constructed of polycarbonate.

5. An apparatus for enclosing a non-sterile video camera, its trailing cable, and a camera coupler in a sterile enclosure for use of the camera in the sterile environment of an operating room, the camera being attachable to an endoscope via the coupler, said apparatus comprising:
   a generally cylindrical drape member having an open proximal end for receiving an unsterile camera, its associated cables, and a camera coupler, and a closed distal end providing a barrier between the camera coupler and the endoscope, said proximal end constructed of a flexible and substantially non-elastic material, said distal end constructed of a flexible and substantially elastic material; and
   an optically clear window mounted in said distal end of said drape which is contactable by the camera coupler when positioned inside said drape for coupling to the endoscope.

6. An apparatus, as claimed in claim 5, wherein said distal end is constructed of polyurethane.

7. An apparatus, as claimed in claim 5, wherein said window further includes:
   filter means for selectively filtering wavelengths of light passing through said window.

8. An apparatus, as claimed in claim 5, wherein:
   said window is constructed of polycarbonate.

* * * * *